(12) United States Patent
Church et al.

(10) Patent No.: US 9,005,977 B2
(45) Date of Patent: Apr. 14, 2015

(54) METHODS AND COMPOSITIONS FOR LIMITING VIABILITY OF A MODIFIED HOST CELL OUTSIDE OF DESIGNATED PROCESS CONDITIONS

(75) Inventors: George Church, Brookline, MA (US); Frank A. Skraly, Watertown, MA (US); Brian D. Green, Watertown, MA (US); Jacob C. Harrison, Newton, MA (US)

(73) Assignee: Joule Unlimited Technologies, Inc., Cambridge, MA (US)

( * ) Notice: Subject to any disclaimer, the term of this patent is extended or adjusted under 35 U.S.C. 154(b) by 508 days.

(21) Appl. No.: 13/238,262

(22) Filed: Sep. 21, 2011

(65) Prior Publication Data

US 2012/0077273 A1 Mar. 29, 2012

Related U.S. Application Data

(60) Provisional application No. 61/385,142, filed on Sep. 21, 2010.

(51) Int. Cl.
| | | |
|---|---|---|
| *C12N 9/00* | (2006.01) | |
| *C12N 1/20* | (2006.01) | |
| *C12N 15/00* | (2006.01) | |
| *C12N 15/74* | (2006.01) | |
| *C07H 21/04* | (2006.01) | |
| *C12N 15/63* | (2006.01) | |
| *C07K 14/435* | (2006.01) | |
| *C12N 13/00* | (2006.01) | |

(52) U.S. Cl.
CPC .............. *C12N 15/63* (2013.01); *C07K 14/435* (2013.01); *C12N 13/00* (2013.01)

(58) Field of Classification Search
None
See application file for complete search history.

(56) References Cited

U.S. PATENT DOCUMENTS 7,183,097 B1 2/2007 Gerdes et al.

OTHER PUBLICATIONS

Chica et al. Curr Opin Biotechnol. Aug. 2005;16(4):378-84.*
Hitomi, K. et al., "Bacterial Cryptochrome and Photolyase: Characterization of Two Photolyase-like Genes of *Synechocystis* sp. PCC6803," Nucleic Acids Research, 2000, pp. 2353-2362, vol. 28, No. 12.
J. Craig Venter Institute, "General Information for *Synechococcus* elongates PCC 7942," Apr. 18, 2006, two pages [Online] [Retrieved Mar. 21, 2012] Retrieved from the Internet <URL:http://cmr.jcvi.org/tigr-scripts/CMR/GenomePage.cgi?org+ntse03.>.
Melnikov, O. et al.,"Site-specific Recombination in the Cyanobacterium *Anabaena* sp. Strain Pcc 7120 Catalyzed by the Integrase of Coliphage HK022," *Journal of Bacteriology*, 2009, pp. 4458-4464, vol. 191, No. 13, and p. 5879, Erratum, vol. 191, No. 18.
Ogawa, T., "A Gene Homologous to the Subunit-2 Gene of NADH Dehydrogenase Is Essential to inorganic Carbon Transport of *Synechocystis PCC6803*," *Proceedings of the National Academy of Science, USA*, May 1991, pp. 4275-4279, vol. 88.
PCT International Search Report and Written Opinion, PCT Application No. PCT/US2011/052606, Apr. 11, 2012, eleven pages.
Van Houten, B. et al.,"'Close-fitting sleeves': DNA Damage Recognition by the UvrABC Nuclease System," *Mutation Research*, 2005, pp. 92-117, vol. 577.
Williams, J.G. et al., "Stable Integration of Foreign DNA into the Chromosome of the Cyanobacterium *Synechococcus* R2," *Gene*, Sep. 1983, one page. [Online] [Retrieved Mar. 21, 2012] Retrieved from the Internet <URL:http://www.ncbi.nlm.nih.gov/pubmed/6414889.>.

* cited by examiner

*Primary Examiner* — Christian Fronda
(74) *Attorney, Agent, or Firm* — Fenwic & West LLP; Chang B. Hong

(57) ABSTRACT

The invention provides methods and compositions for inhibiting proliferation of a modified host cell outside of a designated process condition. Compositions and methods for providing a host cell having reduced viability when exposed to natural conditions external to a controlled environment are disclosed.

7 Claims, No Drawings

METHODS AND COMPOSITIONS FOR LIMITING VIABILITY OF A MODIFIED HOST CELL OUTSIDE OF DESIGNATED PROCESS CONDITIONS

CROSS-REFERENCE TO RELATED APPLICATIONS

This application claims priority to earlier filed U.S. Provisional Patent Application No. 61/385,142, filed Sep. 21, 2010.

FIELD OF THE INVENTION

The present disclosure relates to the field of molecular biology, and more particularly to methods and compositions for limiting viability of a modified host cell outside of designated process conditions.

BACKGROUND OF THE INVENTION

The use of genetically engineered microbes can offer enormous potential benefits. Genetically modified organisms can be used industrially to produce a wide range of fuels and chemicals using $CO_2$ as a carbon source, water as an electron source, and sunlight as an energy source. Some caution is warranted, however, because information about the ecology and evolution of transgenic microbes in the wild is limited, Microbes occur in extremely large populations with short generation times, so they adapt quickly to adverse conditions, Bacteria also can transfer DNA into unrelated microbes, and the long-term ecological consequences of that transfer are unclear (Bushman, 2002). The con sequences of releasing transgenic microbes into the environment have not been evaluated adequately. It is desirable to take precautions to prevent robust viability of a genetically modified organism outside of a controlled growth environment, e.g., to prevent or mitigate untoward environmental consequences following inadvertent release of a genetically modified organism into the wild.

SUMMARY OF THE INVENTION

The present invention relates to methods and compositions for limiting viability of a cell outside of a designated process or preselected set of process conditions. The invention provides, in certain embodiments, a method for altering cell viability, comprising the steps of: selecting a non-nutrient ambient process condition for use with the cell, wherein the process condition is present in a controlled environment and absent outside the controlled environment; and genetically modifying the cell, wherein the genetic modification decreases cell viability in response to the absence of the process condition. Certain embodiments of the invention provide for a cell, genetically modified to have decreased viability outside of a preselected non-nutrient ambient process condition. In one aspect, the cell has been genetically modified to reduce the expression of a gene, wherein the reduction of the expression of the gene decreases the viability of the cell outside of the preselected process condition.

In one aspect of the invention, the process condition is selected from the group consisting of: a preselected amount of electromagnetic radiation; a preselected amount of moisture content; a preselected pH range; a preselected amount of a chemical inducer; a preselected level of $CO_2$; and a preselected temperature range. In a further embodiment, the electromagnetic radiation is ultraviolet radiation or infrared radiation.

In one embodiment of the invention, the cell is a photoautotroph. In another embodiment of the invention, the cell is a cyanobacterium or algae.

In one aspect, the genetically modified cell has a reduced expression of an engineered nucleic acid. In a further aspect, the nucleic acid is endogenous. In a still further aspect, the endogenous nucleic acid has been excised from the genome of the cell. In yet another aspect, the excised nucleic acid is selected from the group consisting of: a DNA repair pathway nucleic acid, a desiccation tolerance nucleic acid, a carbon concentrating mechanism nucleic acid, an engineered thermotolerance nucleic acid, an engineered pH tolerance nucleic acid, and an engineered flue gas dependence nucleic acid.

In one embodiment of the invention, the genetic modification reduces expression of a gene that encodes an enzyme that acts on a nucleic acid substrate. In another embodiment, the enzyme repairs ultraviolet radiation-induced damage. In a further embodiment, the gene is selected from Table 1. In an alternative embodiment, the gene is selected from a group of *Synechococcus elongatus* genes consisting of: phr, phrA, uvrA, uvrB, uvrC, perA, mutM, mutY, radA, recG, mfd, and radC. In another embodiment, the activity of the enzyme is selected from the group consisting of: deoxyribopyrimidine photolyase, DNA photolyase, excinuclease, DNA-dependent ATPase, helicase, formamidopyrimidine-DNA glycosylase, A/G-specific adenine glycosylase, DNA recombination, ATP-dependent DNA helicase, transcription repair coupling, and DNA repair.

In another embodiment of the invention, the genetic modification reduces expression of a gene that encodes an enzyme that is part of a carbon concentrating mechanism. In one aspect, the enzyme is part of a carbon-fixing pathway or a carbon-concentrating mechanism. In another aspect, the gene is selected from Table 2. In yet another aspect, the gene is selected from the group of *Synechococcus elongatus* genes consisting of: ndhB, sbtA, nicA, ccmK1, ccmK2, ccmK3, ccmK4, ccmL, ccmM, and ccmN. In still another aspect, the activity of the enzyme is selected from the group consisting of: NAD(P)H-quinone oxidoreductase, sodium-dependent bicarbonate transporter, bicarbonate transporter, and carbon dioxide concentrating mechanism.

The invention also provides for methods and compositions using genetically modified cells, where the genetic modification reduces expression of an endogenous or exogenous gene in the cell. The genetic modification comprises a gene knock out, in one aspect. In another aspect, the genetic modification comprises a gene excision. In a further aspect, the gene excision is performed by the λatt system. In an alternative further aspect, the gene excision is performed by the HK022 Int protein. In another aspect of the invention, the gene excision is performed by natural transformation and homologous recombination.

In another embodiment of the invention, the genetic modification comprises a gene insertion. In one embodiment, the gene insertion is introduced via site-specific integration. In a further embodiment, the site-specific integration is performed by a bacteriophage. In an alternative further embodiment, the site-specific integration proceeds via the activity of an Int protein.

The present invention provides for a cell comprising a genetic modification of a gene selected from Table 1, wherein the genetic modification reduces expression of the gene and reduces viability of the cell outside of a preselected amount of ultraviolet radiation.

The present invention also provides for an engineered cell, the cell comprising: at least one engineered nucleic acid selected from the group consisting of: a DNA repair pathway nucleic acid; a pH tolerance nucleic acid; a flue gas dependence nucleic acid; a salt tolerance nucleic acid; and a carbon-concentrating mechanism pathway nucleic acid; wherein the engineered cell downregulates an endogenous protein as a result of the engineered nucleic acid, or has a gene knocked-out as a result of the engineered nucleic acid.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999).

All publications, patents and other references mentioned herein are hereby incorporated by reference in their entireties for all purposes.

The following terms, unless otherwise indicated, shall be understood to have the following meanings:

Engineered nucleic acid: An "engineered nucleic acid" is a nucleic acid molecule that includes at least one difference from a naturally-occurring nucleic acid molecule. An engineered nucleic acid includes all exogenous modified and unmodified heterologous sequences (i.e., sequences derived from an organism or cell other than that harboring the engineered nucleic acid) as well as endogenous genes, operons, coding sequences, or non-coding sequences, that have been modified, mutated, or that include deletions or insertions as compared to a naturally-occurring sequence. Engineered nucleic acids also include all sequences, regardless of origin, that are linked to an inducible promoter or to another control sequence with which they are not naturally associated. Engineered nucleic acids further include all sequences that can be used to down-regulate or knock out expression of an endogenous gene. These include anti-sense molecules, RNAi molecules, constructs for producing homologous recombination, cre-lox constructs, and the like.

DNA repair pathway nucleic acid: A "DNA repair pathway nucleic acid" or "UV tolerance nucleic acid" refers to a nucleic acid that alone or in combination with another nucleic acid encodes a protein whose overexpression, downregulation, or inhibition results in a change in viability of a cell in the presence of ultraviolet electromagnetic radiation. This change can decrease viability of a cell outside of a preselected process condition with low levels of UV radiation compared to outside of the preselected process condition. Exemplary DNA repair pathway nucleic acids are provided in Table 1. A DNA repair pathway nucleic acid further includes a nucleic acid used to reduce the expression of or knock out one or more endogenous genes whose expression affects viability in the presence of UV radiation or DNA repair.

Desiccation tolerance nucleic acid: A "desiccation tolerance nucleic acid" refers to a nucleic acid that alone or in combination with another nucleic acid encodes a protein whose overexpression, downregulation, or inhibition, results in a change in viability of a cell in the presence of low atmospheric humidity conditions. This change can decrease viability of a cell outside of a preselected process condition with high levels of moisture content compared to outside of the preselected process condition. A desiccation tolerance nucleic acid further includes a nucleic acid used to reduce the expression of or knock out one or more endogenous genes whose expression affects viability in the presence of low moisture content.

Carbon concentrating mechanism nucleic acid: A "carbon concentration mechanism nucleic acid" refers to a nucleic acid that alone or in combination with another nucleic acid encodes a protein whose overexpression, downregulation, or inhibition, results in a change in viability of a cell in the presence of certain $CO_2$ level conditions. This change can decrease viability of a cell outside of a preselected process condition with high levels of $CO_2$ compared to outside of the preselected process condition. Exemplary carbon concentrating mechanism nucleic acids are provided in Table 2. A carbon concentrating mechanism nucleic acid further includes a nucleic acid used to reduce the expression of or knock out one or more endogenous genes whose expression affects viability in the presence of low or natural $CO_2$ levels outside of a preselected process condition.

Thermotolerance nucleic acid: A "thermotolerance nucleic acid" refers to a nucleic acid that alone or in combination with another nucleic acid encodes a protein whose overexpression, downregulation, or inhibition results in a change in thermotolerance. This change can decrease viability outside of a preselected process condition temperature range. Exemplary thermotolerance nucleic acids include those encoding ClpC/Hsp100, groESL1, HspA, and PsbU. A thermotolerance nucleic acid further includes a nucleic acid used to reduce the expression of or knock out one or more endogenous genes whose expression affects thermotolerance.

pH tolerance nucleic acid: A "pH tolerance nucleic acid" refers to a nucleic acid that alone or in combination with another nucleic acid encodes a protein whose overexpression, downregulation, or inhibition affects viability at pH levels outside of a preselected process condition. Exemplary pH tolerance nucleic acids include those encoding glutamate decarboxylase and superoxide dismutase. A pH tolerance nucleic acid further includes a nucleic acid used to reduce the expression of or knock out one or more endogenous genes whose expression affects pH tolerance.

Flue gas dependence nucleic acid: A "Flue gas dependence nucleic acid" refers to a nucleic acid that alone or in combination with another nucleic acid encodes a protein whose overexpression, downregulation, or inhibition affects viability outside a preselected process condition including flue gas components including carbon dioxide, $SO_x$, $NO_x$, and $N_2$, where x is 1 or 2. A flue gas tolerance nucleic acid further includes a nucleic acid used to reduce the expression of or knock out one or more endogenous genes whose expression affects flue gas dependence or tolerance outside of a preselected flue gas condition.

Endogenous: As used herein with reference to a nucleic acid molecule and a particular cell or microorganism refers to a nucleic acid sequence or peptide that is in the cell and was not introduced into the cell using recombinant engineering techniques. For example, a gene that was present in the cell when the cell was originally isolated from nature is considered to be endogenous. A gene is still considered endogenous if the control sequences, such as a promoter or enhancer sequences that activate transcription or translation have been altered through recombinant techniques.

Exogenous: As used herein with reference to a nucleic acid molecule and a particular cell or microorganism refers to a nucleic acid sequence or peptide that was not present in the cell when the cell was originally isolated from nature. For example, a nucleic acid that originated in a different microorganism and was engineered into an alternate cell using recombinant DNA techniques or other methods for delivering said nucleic acid is considered to be exogenous.

Expression: The process by which a gene's coded information is converted into the molecules that support the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Overexpression: Overexpression refers to any state in which a gene is caused to be transcribed at a net elevated rate as compared to the net endogenous transcription rate for that gene. In some examples, overexpression additionally includes a net elevated rate of translation of the gene compared to the endogenous translation rate for that gene. Net, in this context, refers to the net balance between forward and reverse reactions, e.g., between message transcription and message breakdown, or protein translation and protein degradation. Methods of testing for overexpression are well known in the art, for example transcribed RNA levels can be assessed using reverse transcriptase polymerase chain reaction (RT-PCR) and protein levels can be assessed using sodium dodecyl sulfate polyacrylamide gel electrophoresis (SDS-PAGE) analysis. Furthermore, a gene is considered to be overexpressed when it exhibits elevated activity compared to its endogenous activity, which may occur, for example, through reduction in concentration or activity of its inhibitor, or via expression of mutant version with elevated activity. In preferred embodiments, when the host cell encodes an endogenous gene with a desired biochemical activity, it is useful to overexpress an exogenous gene, which allows for more explicit regulatory control in the bioprocessing and a means to potentially mitigate the effects of central metabolism regulation, which is focused around the native genes explicitly.

Downregulation: Downregulation refers to any state in which a gene is caused to be transcribed at a net reduced rate compared to the endogenous gene transcription rate for that gene. In certain embodiments, gene expression is downregulated via expression of nucleic acids, such as antisense oligonucleotides, double-stranded RNA, small interfering RNA, small hairpin RNA, microRNAs, ribozymes, and the like. In some examples, downregulation additionally includes a net reduced level of translation of the gene compared to the endogenous translation rate for that gene. Furthermore, a gene is considered to be downregulated when it exhibits decreased activity compared to its endogenous activity, which may occur, for example, through an increase in concentration or activity of its inhibitor, or via expression of mutant version with reduced activity. Methods of testing for downregulation are well known to those in the art, for example the transcribed RNA levels can be assessed using RT-PCR and proteins levels can be assessed using SDS-PAGE analysis.

Knock-out: A gene whose level of expression or activity has been reduced to zero. In some examples, a gene is knocked-out via deletion or replacement of some or all of its coding sequence. In other examples, a gene is knocked-out via introduction or removal of one or more nucleotides into its open-reading frame, which results in translation of a nonsense or otherwise non-functional protein product.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising," used in association with a group of integers will be understood to imply the inclusion of a stated integer or group of integers but not the exclusion of any other integer or group of integers.

Selected or Engineered Microorganisms

Microorganism: Includes prokaryotic and eukaryotic microbial species from the Domains *Archaea, Bacteria* and *Eucarya*, the latter including yeast and filamentous fungi, protozoa, algae, or higher Protista. The terms "microbial cells" and "microbes" are used interchangeably with the term microorganism.

A variety of organisms can be transformed to produce a product of interest and also engineered to limit viability outside of a preselected process condition. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

The cell can be a Gram-negative bacterial cell or a Gram-positive bacterial cell. A Gram-negative host cell of the invention can be, e.g., *Gluconobacter, Rhizobium, Bradyrhizobium, Alcaligenes, Rhodobacter, Rhodococcus. Azospirillum, Rhodospirillum, Sphingomonas, Burkholderia, Desuifomonas, Geospirillum, Succinomonas, Aeromonas, Shewanella, Halochromatium, Citrobacter, Escherichia, Klebsiella, Zymomonas Zymobacter*, or *Acetobacter*. A Gram-positive host cell of the invention can be, e.g., *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, or *Sarcina*.

Extremophiles are also contemplated as suitable organisms for limiting viability outside of a preselected process conditions. Such organisms withstand various process conditions such as temperature, radiation, pressure, gravity, vacuum, desiccation, salinity, pH, oxygen tension, and chemicals, but may have decreased viability outside of these process conditions. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation-tolerant organisms include *Deinococcus radiodurans*. Pressure-tolerant organisms include piezophiles or barophiles, which tolerate pressure of 130 MPa. Hypergravity—(e.g., >1 g) and hypogravity—(e.g., <1 g) tolerant organisms are also contemplated. Vacuum-tolerant organisms include tardigrades, insects, microbes and seeds. Dessicant-tolerant and anhydrobiotic organisms include xerophiles such as *Artemia salina*; nematodes, microbes, fungi and lichens. Salt-tolerant organisms include halophiles (e.g., 2-5 M NaCl) *Halobacteriacea* and *Dunaliella salina*. pH-tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas-tolerant organisms, which tolerate pure $CO_2$ include *Cyanidium caldarium* and metal-tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments*. New York: Plenum (1998) and Seckbach, J. "Search for Life in the Universe with Terrestrial Microbes Which Thrive Under Extreme Conditions." In Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea*.

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spennatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis, and Zygonium.

Green non-sulfur bacteria include but are not limited to the following genera: *Chloroflexus, Chloronema, Oscillochloris, Heliothrix, Herpetosiphon, Roseiflexus*, and *Thermomicrobium*.

Green sulfur bacteria include but are not limited to the following genera: *Chlorobium, Clathrochloris*, and *Prosthecochloris*.

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus*, and *Thiocystis*.

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira*.

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

*Archaeobacteria* include but are not limited to methanogenic *archaeobacteria* such as *Methanobacterium* sp., *Methanobrevibacter* sp., *Methanothennus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic sulfur-metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

In some cases, the cell genetically modified to have limited viability will have undergone hyperphotosynthetic conversion. Hyperphotosynthetic conversion requires extensive genetic modification; thus, in some embodiments the parental photoautotrophic organism can be transformed with exogenous DNA.

Organisms for hyperphotosynthetic conversion include: *Arabidopsis thaliana, Panicum virgatum, Miscanthus giganteus,* and *Zea mays* (plants), *Botryococcus braunii, Chlamydomonas reinhardtii* and *Dunaliela salina* (algae), *Synechococcus* sp. PCC 7002, *Synechococcus* sp. PCC 7942, *Synechocystis* sp. PCC 6803, and *Thermosynechococcus elongatus* BP-1 (cyanobacteria), *Chlorobium tepidum* (green sulfur bacteria), *Chloroflexus auranticus* (green non-sulfur bacteria), *Chromatium tepidum*, and *Chromatium vinosum* (purple sulfur bacteria), *Rhodospirillum rubrum, Rhodobacter capsulatus*, and *Rhodopseudomonas palusris* (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms for genetically modifying to limit viability outside of a preselected process condition include microorganisms that can be engineered to fix carbon dioxide bacteria such as *Escherichia coli, Acetobacter aceti, Bacillus subtilis*, yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens*, or *Zymomonas mobilis*.

Disruption of Endogenous DNA sequences

In certain instances, chromosomal DNA sequence native (i.e., "endogenous") to the host organism are altered. Manipulations are made to non-coding regions, including promoters, ribosome binding sites, transcription terminators, and the like to increase or decrease expression of specific gene product(s). In alternate embodiments, the coding sequence of an endogenous gene is altered to affect stability, folding, activity, or localization of the intended protein. Alternately, specific genes can be entirely deleted or "knocked-out." Techniques and methods for such manipulations are known to those skilled in the art [Nelson J A, and Lefebvre P A. "Targeted disruption of the NIT8 gene in *Chlamydomonas reinhardtii*." Mol Cell Bio (1995). 15(10):5762-5769; Hanson T E and Tabita F R. "A ribulose-1,5-bisphosphate carboxylase/oxygenase (RubisCO)-like protein from *Chlorobium tepidum* that is involved with sulfur metabolism and the response to oxidative stress." Proc Natl Acad Sci (2001). 98(8):4397-4402; Sugita C, Mutsuda M, Sugiura M, Sugita M. "Targeted deletion of genes for eukaryotic RNA-binding proteins, Rbp1 and Rbp2, in the cyanobacterium *Synechococcus* sp. Strain PCC7942: Rbp1 is indispensable for cell growth at low temperatures." FEMS Microbiol Letters (1999). 176(1): 155-161; Kirilovsky D, Roncel M, Boussac A, Wilson A, Zurita J L, Ducruet J, Bottin H, Sugiura M, Ortega J M, Rutherford A W. "Cytochrome c550 in the cyanobacterium *Thermosynechococcus elongatus*. Study of Redox mutants." J Biol Chem (2004). 279(51):52869-80; Datsenko K A, Wanner B L. PNAS (2000). "One-step inactivation of chromosomal genes in *E. coli* K-12 using PCR Products." 97: 6640-6645; Link A J et al. J Bacteriol (1997). "Methods for generating precise deletions and insertions in the genome of wild-type *Escherichia coli*: Application to open reading frame characterization." 179:6228-6237; Baba T et al. Mol Syst Biol (2006). Construction of *Escherichia coli* K-12 in-frame, single gene knockout mutants: the Keio collection." 2:2006.0008; Tischer B K, von Einem J, Kaufer B, Osterrieder N. Biotechniques (2006). "Two-step red-mediated recombination for versatile high-efficiency markerless DNA manipulation in *Escherichia* coli." 40(2):191-7.; McKenzie G J, Craig N L. BMC Microbiol (2006). Fast, easy and efficient: site-specific insertion of transgenes into enterobacterial chromosomes using Tn7 without need for selection of the insertion event." 6:39].

In certain embodiments, post-transcriptional gene silencing (PTGS) is employed to reduce the expression level of an endogenous gene via expression of a heterologous RNA sequence, frequently antisense to the gene requiring disruption [Lechtreck K, Rostmann J, and Grunow A. "Analysis of *Chlamydomonas* SF-assemblin by GFP tagging and expression of antisense constructs." J. Cell Sci (2002). 115:1511-1522; Smith N A, Singh S P, Wang M, Stotjesdijk P A, Green A G, and Waterhouse P M. "Total silencing by intron-spliced hairpin RNAs." Nature (2000). 407:319-320; Furhmann M, Stahlberg A, Govorunova E, Rank S, and Hegeman P. "The abundant retinal protein of the *Chlamydomonas* eye is not the photoreceptor for phototaxis and photophobic responses." J. Cell Sci (2001). 114:3857-3863; Rohr J, Sarkar N, Balenger S Jeong B R, Cerutti H. "Tandem inverted repeat system for selection of effective transgenic RNAi strains in *Chlamydomonas*" Plant J (2004). 40(4):611-21].]

In other embodiments, expression of naturally encoded or exogenous small RNA or microRNA species is employed to downregulate endogenous gene expression [Molnar A, Schwach F, Studholme D J, Tgyenemann E C, and Baulcombe D C. "miRNAs control gene expression in the single-cell alga *Chlamydomonas reinhardtii*." Nature (2007). 447 (7148):1126-9; Zhao T, Li G, Mi S, Li S, Hannon G J, Wang X J, Qi Y. "A complex system of small RNAs in the unicellular green alga *Chlamydomonas reinhardtii*." Genes Dev (2007). 21(10):1190-203].

Propagation of Selected Microorganisms

Methods for cultivation of photosynthetic organisms in liquid media and on agarose-containing plates are well known to those skilled in the art (see, e.g., websites associated with ATCC, and with the Institute Pasteur). For example, *Synechococcus* sp. PCC 7002 cells (available from the Pasteur Culture Collection of Cyanobacteria) are cultured in BG-11 medium (17.65 mM NaNO3, 0.18 mM K2HPO4, 0.3 mM MgSO4, 0.25 mM CaCl2, 0.03 mM citric acid, 0.03 mM ferric ammonium citrate, 0.003 mM EDTA, 0.19 mM Na2CO3, 2.86 mg/L H3BO3, 1.81 mg/L MnCl2, 0.222 mg/L ZnSO4, 0.390 mg/L Na2MoO4, 0.079 mg/L CuSO4, and 0.049 mg/L Co(NO3)2, pH 7.4) supplemented with 16 µg/L biotin, 20 mM MgSO4, 8 mM KCl, and 300 mM NaCl (see, e.g., website associated with the Institute Pasteur, and Price G D, Woodger F J, Badger M R, Howitt S M, Tucker L. "Identification of a SulP-type bicarbonate transporter in marine cyanobacteria. Proc Natl. Acad. Sci. USA (2004) 101(52): 18228-33). Typically, cultures are maintained at 28° C. and bubbled continuously with 5% CO2 under a light intensity of 120 µmol photons/m2/s. Alternatively, as described in Example 1, *Synechococcus* sp. PCC 7002 cells are cultured in A$^+$ medium as previously described [Frigaard N U et al. (2004) "Gene inactivation in the cyanobacterium *Synechococcus* sp. PCC 7002 and the green sulfur bacterium *Chlorobium tepidum* using in vitro-made DNA constructs and natural transformation," Methods Mol. Biol., 274:325-340].

The above define typical propagation conditions. As appropriate, incubations are performed using alternate media or gas compositions, alternate temperatures (5-75° C.), and/or light fluxes (0-5500 µmol photons/m2/s).

Light is delivered through a variety of mechanisms, including natural illumination (sunlight), standard incandescent, fluorescent, or halogen bulbs, or via propagation in specially-designed illuminated growth chambers (for example Model LI15 Illuminated Growth Chamber (Sheldon Manufacturing, Inc. Cornelius, Oreg.). For experiments requiring specific wavelengths and/or intensities, light is distributed via light emitting diodes (LEDs), in which wavelength spectra and intensity can be carefully controlled (Philips).

Carbon dioxide is supplied via inclusion of solid media supplements (i.e., sodium bicarbonate) or as a gas via its distribution into the growth incubator or media. Most experiments are performed using concentrated carbon dioxide gas, at concentrations between 1 and 30%, which is directly bubbled into the growth media at velocities sufficient to provide mixing for the organisms. When concentrated carbon dioxide gas is utilized, the gas originates in pure form from commercially-available cylinders, or preferentially from concentrated sources including off-gas or flue gas from coal plants, refineries, cement production facilities, natural gas facilities, breweries, and the like.

Exemplary methods and materials are described below, although methods and materials similar or equivalent to those described herein can also be used in the practice of the invention and will be apparent to those of skill in the art. All publications and other references mentioned herein are incorporated by reference in their entirety for all purposes. In case of conflict, the present specification, including definitions, will control. The materials, methods, and examples are illustrative only and not intended to be limiting.

Example 1

Genetically Modified Organisms Sensitive to Ultraviolet (UV) Radiation

Under controlled production conditions of a photosynthetic organism, UV radiation is filtered out of the incident radiation, but in the wild, UV exposure is unavoidable in the normal course of exposure to unfiltered sunlight. Mutations in the genes provided in Table 1 confer UV sensitivity. Prior to entering an industrial process, the organism is engineered to have reduced expression of a gene from Table 1. The engineered organism is robustly viable only under the controlled conditions of the process. In one embodiment, engineered organism maintains a gene from Table 1 until a designated treatment is given, i.e., exposure to the presence or absence of a certain chemical inducer, exposure to a defined temperature profile, etc.

Genes specific for UV resistance, such as those encoding photolyase, are selected for deletion. Genes are excised using a specific and complete excision method such as the λatt system of the λ bacteriophage, described below. *Synechococcus elongatus* PCC 7002 possesses one apparent photolyase phr (SYNPCC7002_A2796). Removal of this gene renders the organism unable to repair UV-induced pyrimidine dimers. Photolyases repair only this specific kind of damage, which is induced only by UV radiation. In other selected organisms uvrA is deleted, rendering the organism susceptible to mutation induced by UV radiation, among other causes (B. van Houten, et al., 'Close-fitting sleeves': DNA damage recognition by the UvrABC nuclease system. *Mutat. Res.* 577:92-117 (2005)).

TABLE 1

Gene targets in *E. Coli* and *Synechococcus* sp. PCC 7002 for mutation or excision to confer UV sensitivity.

| E. coli gene | Synechococcus sp. PCC 7002 homolog | Enzyme Activity |
| --- | --- | --- |
| phr (b0708) | A2796 (phr) | deoxyribopyrimidine photolyase |
| phr (b0708) | A2668 (phrA) | DNA photolyase |
| uvrA (b4058) | A1468 (uvrA) | excinuclease ABC (A subunit) |
| uvrB (b0779) | A2255 (uvrB) | excinuclease ABC (B subunit) |
| uvrC (b1913) | A0237 (uvrC) | excinuclease ABC (C subunit) |
| uvrD (b3813) | A0531 (pcrA) | DNA-dependent ATPase I and helicase II |
| mutM (b3635) | A1816 (mutM) | formamidopyrimidine-DNA glycosylase |
| mutY (b2961) | A2741 (mutY) | A/G-specific adenine glycosylase |
| radA (b4389) | A0978 (radA) | DNA recombination protein |
| recG (b3652) | A1856 (recG) | ATP-dependent DNA helicase |
| mfd (b1114) | A1287 (mfd) | transcription repair coupling factor |
| N/A | A0220 (radC) | DNA repair protein |

Example 2

Genetically Modified Organisms Requiring High Levels of $CO_2$

Under controlled production conditions of a photosynthetic organism, higher levels of $CO_2$ are present than in the wild. Mutations in the genes provided in Table 2 decrease the ability of a cell to fix carbon from $CO_2$ and render the cell unable to grow outside of the process condition. Prior to entering an industrial process, the organism is engineered to have reduced expression of a gene from Table 2. The engineered organism is robustly viable only under the controlled conditions of the process. In one embodiment, engineered organism maintains a gene from Table 2 until a designated treatment is given, i.e., exposure to the presence or absence of a certain chemical inducer, exposure to a defined temperature profile, etc.

TABLE 2

Gene targets in *Synechococcus* sp. PCC 7002 for mutation or excision to reduce viability in natural $CO_2$ conditions.

| Locus | Genes(s) | Enzyme Activity |
| --- | --- | --- |
| SYNPCC7002_A2547 | ndhB | NAD(P)H-quinone oxidoreductase |
| SYNPCC7002_A0470 | sbtA | sodium-dependent bicarbonate transporter |
| SYNPCC7002_A2371 | bicA | bicarbonate transporter |
| SYNPCC7002_A1802-3 | ccmK1, ccmK2 | carbon dioxide concentrating mechanism protein |
| SYNPCC7002_A2612-3 | ccmK3, ccmK4 | carbon dioxide concentrating mechanism protein |
| SYNPCC7002_A1801 | ccmL | carbon dioxide concentrating mechanism protein |
| SYNPCC7002_A1800 | ccmM | carbon dioxide concentrating mechanism protein |
| SYNPCC7002_A1799 | ccmN | carbon dioxide concentrating mechanism protein |

Genes specific for carbon fixation, such as those involved in carbon dioxide concentrating mechanism, are selected for deletion. Genes are excised using a specific and complete excision method such as the λatt system of the λ bacteriophage, described below.

Overexpression of genes to reduce cell viability outside of the designated process condition is also performed via conventional genetic engineering techniques. Carbonic anhydrase is overexpressed in the cytosol of a cell, such as *Synechococcus* sp. PCC 7002, resulting in a high $CO_2$ requiring phenotype. The engineered cell has a decreased viability outside of the preselected process condition of a high $CO_2$ levels.

Example 3

Methods for Genetically Modifying Organisms to Insert a Gene of Interest

Controllable Site-Specific Integration into and Excision from the Host Chromosome Using a Bacteriophage.

Many bacteriophages, in particular λ-like bacteriophage, are capable of site-specific integration into and excision from the host chromosome. Integration generally requires the activity of a single protein, Int, which recognizes 2 pairs of recombination sequences (attL and attR), one pair of which resides on the phage chromosome and the other on the host chromosome. Recombination between these pairs of sequences creates a pair of hybrid sequences consisting of phage and chromosome sequences. Excision of the phage from the host generally requires at least one additional phage protein in addition, Xis, as well as the host encoded protein IHF, that allow the cell to recombine at the hybrid phage/chromosome sequence. The Int protein from bacteriophage HK022, which is similar to λ, has been shown to promote the integration and excision at specific sites without the requisite Xis and IHF. Recently, Int-catalyzed site-specific recombination has been demonstrated in the cyanobacterium *Anabaena* sp. PCC7120 (O. Melnikov, et al., Site-specific recombination in the cyanobacterium *Anabaena* sp. Strain PCC7120 catalyzed by the integrase of coliphage HK022. *J. Bacteriol.* 191:4458-4464 (2009)).

Genes Flanked by Recombination Sequences.

To control the removal of gene(s) that confer UV resistance or $CO_2$ fixation, genes are cloned such that they are flanked by recombination sequences which are recognized by the HK022 Int protein. A copy of the HK022 int gene is cloned into the chromosome of the production host and expression of the protein is controlled by an inducible promoter. Examples of inducible promoters can include, but are not limited to, the nickel-inducible P(nrs) from *Synechocystis* sp. PCC 6803, the ammonia-repressible P(nirA) from *Synechococcus* sp. PCC 7942, and the synthetic and IPTG-inducible P(tac).

Excision of Genes by Natural Transformation and Homologous Recombination.

Alternatively, genes are excised by natural transformation and homologous recombination in many cyanobacterial hosts using standard transformation protocols. For example, in the case of *Synechococcus elongatus* sp. PCC7002: 5-10 μg of plasmid DNA is added to 1 ml of neat cyanobacterial culture that has been grown to an OD-730 of approximately 1.0. The cell-DNA mixture is incubated at 37° C. for 4 hours in the dark in a closed tube with gentle mixing, plated onto A+ agar plates, and incubated at 37° C. in a photoincubator (Percival) for 24 hours at about 100 μmol photons $m^{-2} s^{-1}$. Subsequently the selective agent is placed under the agar to an appropriate final concentration to diffuse to the cells over the course of 1-2 days. Resistant colonies appear after several days of further incubation. After several further subcultures, segregation of the inserted fragment and complete loss of the wild-type chromosomal sequence is verified by PCR.

What is claimed is:

1. A method for altering viability of a *Synechococcus* cell, comprising the steps of:
   a. providing a non-nutrient ambient process condition for use with said cell, wherein said process condition is present in a controlled environment and absent outside said controlled environment; and
   b. producing a genetically modified cell, wherein the genetically modified cell comprises one or more genetic modifications, wherein said one or more genetic modifications comprises an inactivated phr gene.

2. The method of claim 1, wherein said process condition is selected from the group consisting of: a preselected amount of electromagnetic radiation; a preselected amount of moisture content; a preselected pH range; a preselected amount of a chemical inducer; a preselected level of $CO_2$; and a preselected temperature range.

3. The method of claim 2, wherein said electromagnetic radiation is ultraviolet radiation or infrared radiation.

4. The method of claim 1, wherein said genetic modification reduces expression of the phr gene that encodes an enzyme that acts on a nucleic acid substrate.

5. The method of claim 4, wherein said enzyme repairs UV radiation-induced damage.

6. The method of claim 4, wherein said cell is further modified to inactivate at least a second gene selected from a group of *Synechococcus elongatus* genes consisting of: phr, phrA, uvrA, uvrB, uvrC, perA, mutM, mutY, radA, recG, mfd, and radC.

7. The method of claim 1, wherein said one or more genetic modifications comprises inactivated phr and phrA genes.

* * * * *